(12) United States Patent
Douk et al.

(10) Patent No.: US 7,716,801 B2
(45) Date of Patent: May 18, 2010

(54) LOW-PROFILE DISTAL PROTECTION DEVICE

(75) Inventors: Nareak Douk, Lowell, MA (US);
Nasser Rafiee, Andover, MA (US);
Albert H Dunfee, Byfield, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1638 days.

(21) Appl. No.: 10/718,638

(22) Filed: Nov. 24, 2003

(65) Prior Publication Data
US 2005/0124876 A1    Jun. 9, 2005

(51) Int. Cl.
*B23P 17/00*    (2006.01)
(52) U.S. Cl. .................. 29/419.1; 604/103.06; 606/200
(58) Field of Classification Search .................. 29/447, 29/419.1, 527.1; 606/200, 191; 623/1.15; 604/96.01, 103.06, 523
See application file for complete search history.

(56) References Cited

U.S. PATENT DOCUMENTS

| | | | |
|---|---|---|---|
| 3,521,620 A | 7/1970 | Cook | |
| 3,540,431 A | 11/1970 | Mobin-Uddin | |
| 3,952,747 A | 4/1976 | Kimmell, Jr. | |
| 3,966,938 A | 6/1976 | Ott et al. | |
| 4,080,706 A * | 3/1978 | Heilman et al. | 29/592 |
| 4,425,908 A | 1/1984 | Simon | |
| 4,456,017 A | 6/1984 | Miles | |
| 4,494,531 A | 1/1985 | Gianturco | |
| 4,577,631 A | 3/1986 | Kreamer | |
| 4,619,246 A | 10/1986 | Molgaard-Nielsen et al. | |
| 4,643,184 A | 2/1987 | Mobin-Uddin | |
| 4,662,885 A | 5/1987 | DiPisa, Jr. | |
| 4,664,113 A | 5/1987 | Frisbie et al. | |
| 4,682,599 A | 7/1987 | Konomura | |
| 4,688,553 A | 8/1987 | Metals | |
| 4,719,924 A | 1/1988 | Crittenden et al. | |
| 4,723,549 A | 2/1988 | Wholey et al. | |
| 4,723,936 A | 2/1988 | Buchbinder et al. | |
| 4,727,873 A | 3/1988 | Mobin-Uddin | |
| 4,765,332 A | 8/1988 | Fischell et al. | |
| 4,772,258 A | 9/1988 | Marangoni et al. | |
| 4,790,812 A | 12/1988 | Hawkins, Jr. et al. | |
| 4,793,348 A | 12/1988 | Palmaz | |
| 4,794,928 A | 1/1989 | Kletschka | |

(Continued)

FOREIGN PATENT DOCUMENTS

DE    3417738 A1    11/1985

(Continued)

OTHER PUBLICATIONS

Palestrant, Aubrey M, et al., *Comparative In Vitro Evaluation of the Nitinol Inferior Vena Cava Filter*, Radiology 145:351-355, Nov. 1982.

*Primary Examiner*—David P Bryant
*Assistant Examiner*—Christopher M Koehler

(57) ABSTRACT

A distal protection device captures debris during vascular procedures. In order to reduce the profile of the device, the thickness of the distal protection element is reduced in one or both of the end regions, either by reducing the thickness of filaments which form the distal protection element, or by removing portions of those filaments altogether. Various methods of reducing the thickness of the end regions and different profiles that can be created by the reduction are disclosed.

19 Claims, 7 Drawing Sheets

U.S. PATENT DOCUMENTS

| | | | |
|---|---|---|---|
| 4,817,600 A | 4/1989 | Herms et al. |
| 4,842,579 A | 6/1989 | Shiber |
| 4,848,342 A | 7/1989 | Kaltenbach |
| 4,873,978 A | 10/1989 | Ginsburg |
| 4,921,484 A | 5/1990 | Hillstead |
| 4,926,858 A | 5/1990 | Gifford, III et al. |
| 4,943,297 A | 7/1990 | Saveliev et al. |
| 4,957,501 A | 9/1990 | Lahille et al. |
| 4,990,156 A | 2/1991 | Lefebvre |
| 5,002,560 A | 3/1991 | Machold et al. |
| 5,011,488 A | 4/1991 | Ginsburg |
| 5,041,093 A | 8/1991 | Chu |
| 5,053,008 A | 10/1991 | Bajaj |
| 5,071,407 A | 12/1991 | Termin et al. |
| 5,074,871 A | 12/1991 | Groshong |
| 5,090,960 A | 2/1992 | Don Michael |
| 5,092,839 A | 3/1992 | Kipperman |
| 5,102,415 A | 4/1992 | Guenther et al. |
| 5,108,418 A | 4/1992 | Lefebvre |
| 5,108,419 A | 4/1992 | Reger et al. |
| 5,114,403 A | 5/1992 | Clarke et al. |
| 5,133,733 A | 7/1992 | Rasmussen et al. |
| 5,135,487 A | 8/1992 | Morrill et al. |
| 5,147,379 A | 9/1992 | Sabbaghian et al. |
| 5,152,777 A | 10/1992 | Goldberg et al. |
| 5,160,342 A | 11/1992 | Reger et al. |
| 5,161,427 A | 11/1992 | Fukuda et al. |
| 5,234,458 A | 8/1993 | Metais |
| 5,242,462 A | 9/1993 | El-Nounou et al. |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,358,486 A | 10/1994 | Saab |
| 5,370,657 A | 12/1994 | Irie |
| 5,375,612 A | 12/1994 | Cottenceau et al. |
| 5,376,094 A | 12/1994 | Kline |
| 5,383,887 A | 1/1995 | Nadal |
| 5,397,305 A | 3/1995 | Kawula et al. |
| 5,397,306 A | 3/1995 | Nobuyoshi et al. |
| 5,413,586 A | 5/1995 | Dibie et al. |
| 5,415,630 A | 5/1995 | Gory et al. |
| 5,421,832 A | 6/1995 | Lefebvre |
| 5,480,382 A | 1/1996 | Hammerslag et al. |
| 5,484,424 A | 1/1996 | Cottenceau et al. |
| 5,531,788 A | 7/1996 | Dibie et al. |
| 5,549,626 A | 8/1996 | Miller et al. |
| 5,601,595 A | 2/1997 | Smith |
| 5,626,605 A | 5/1997 | Irie et al. |
| 5,649,953 A | 7/1997 | Lefebvre |
| 5,681,347 A | 10/1997 | Cathcart et al. |
| 5,683,411 A | 11/1997 | Kavteladze et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,758 A | 5/1998 | Nordgren et al. |
| 5,746,767 A | 5/1998 | Smith |
| 5,755,790 A | 5/1998 | Chevillon |
| 5,769,816 A | 6/1998 | Barbut et al. |
| 5,795,322 A | 8/1998 | Boudewijn |
| 5,800,391 A | 9/1998 | Kontos |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,865,800 A | 2/1999 | Mirarchi et al. |
| 5,876,367 A | 3/1999 | Kaganov et al. |
| 5,911,734 A | 6/1999 | Tsugita et al. |
| 5,935,139 A | 8/1999 | Bates |
| 5,972,019 A | 10/1999 | Engelson et al. |
| 6,051,014 A | 4/2000 | Jang |
| 6,066,158 A | 5/2000 | Engelson et al. |
| 6,090,097 A | 7/2000 | Barbut et al. |
| 6,123,715 A | 9/2000 | Amplatz |
| 6,165,200 A | 12/2000 | Tsugita et al. |
| 6,171,327 B1 | 1/2001 | Daniel et al. |
| 6,179,859 B1 | 1/2001 | Bates et al. |
| 6,203,552 B1 | 3/2001 | Bagley et al. |
| 6,235,044 B1 | 5/2001 | Root et al. |
| 6,258,115 B1 | 7/2001 | Dubrul |
| 6,264,672 B1 | 7/2001 | Fisher |
| 6,277,138 B1 | 8/2001 | Levinson et al. |
| 6,277,139 B1 | 8/2001 | Levinson et al. |
| 6,325,815 B1 * | 12/2001 | Kusleika et al. ............ 606/200 |
| 6,325,822 B1 | 12/2001 | Chouinard et al. |
| 6,336,934 B1 * | 1/2002 | Gilson et al. ............... 606/200 |
| 6,346,116 B1 | 2/2002 | Brooks et al. |
| 6,364,895 B1 | 4/2002 | Greenhalgh |
| 6,368,339 B1 | 4/2002 | Amplatz |
| 6,375,670 B1 | 4/2002 | Greenhalgh |
| 6,395,014 B1 | 5/2002 | Macoviak et al. |
| 6,398,773 B1 | 6/2002 | Bagaoisan et al. |
| 6,406,471 B1 | 6/2002 | Jang et al. |
| 6,432,122 B1 | 8/2002 | Gilson et al. |
| 6,602,271 B2 * | 8/2003 | Adams et al. ............... 606/200 |
| 2002/0007210 A1 * | 1/2002 | Chouinard et al. ......... 623/1.15 |
| 2002/0115942 A1 | 8/2002 | Stanford et al. |
| 2004/0158312 A1 | 8/2004 | Chouinard et al. |
| 2006/0015136 A1 * | 1/2006 | Besselink .................. 606/200 |

FOREIGN PATENT DOCUMENTS

| | | |
|---|---|---|
| DE | 3900517 A1 | 7/1989 |
| DE | 4030998 C2 | 11/1995 |
| FR | 2580504 | 10/1986 |
| WO | WO 92/03097 | 3/1992 |
| WO | WO 93/12723 | 7/1993 |
| WO | WO 94/12136 | 6/1994 |
| WO | WO 96/01591 | 1/1996 |
| WO | WO 99/22673 | 5/1999 |
| WO | WO 99/39648 | 8/1999 |
| WO | WO 00/49970 | 8/2000 |
| WO | WO 00/56237 | 9/2000 |

* cited by examiner

LOW-PROFILE DISTAL PROTECTION DEVICE

BACKGROUND OF THE INVENTION

1. Field of the Invention

The present invention relates generally to endovascular devices for capturing particulate during vascular procedures and methods for making same. More particularly, the invention relates to a distal protection element located at the distal end of a delivery member prevent emboli in a blood vessel from moving away from the treatment site during a vascular procedure. The distal protection element is comprised of filaments, some of which have been reduced in thickness during manufacture of the device, so that the device has a low collapsed profile and greater flexibility in the end regions.

2. Related Art

A variety of treatments exist for compressing or removing athersclerotic plaque in blood vessels. The use of an angioplasty balloon catheter is common in the art as a minimally invasive treatment to enlarge a stenotic or diseased blood vessel. This treatment is known as percutaneous transluminal angioplasty (hereinafter, "PTA"). To provide radial support to the treated vessel in order to prolong the positive effects of PTA, a stent may be implanted in conjunction with the procedure.

Thrombectomy is a minimally invasive technique for removal of an entire thrombosis or a sufficient portion of the thrombosis to enlarge a lumen of a stenotic or diseased blood vessel and may be accomplished instead of, or in addition to, a PTA procedure. Atherectomy is another well-known minimally invasive procedure that mechanically cuts or abrades a stenosis within a diseased portion of the vessel. Alternatively, ablation therapies use laser or RF signals to superheat or vaporize the thrombosis within the vessel. Particulate debris loosened during such procedures may be removed from the patient through the catheter.

During each of these procedures, there is a risk that particles dislodged by the procedure will migrate through the circulatory system to embolize distally and cause infarction or strokes. Thus, practitioners have approached prevention of escaped emboli through use of distal protection elements such occlusion devices and filters as well as lysing and aspiration techniques. For example, it is known to remove the particulate material by suction through an aspiration lumen in the treatment catheter or by capturing debris in a filter or occlusion device positioned distal of the treatment area.

Prior art temporary distal protection elements such as filters or occlusion devices are associated with either a catheter or guidewire and are positioned downstream of the area to be treated. One prior art filter arrangement includes a dilatation balloon and a filter mounted on the same catheter. The filter is located distal to the dilatation balloon and consists of a filter material secured to resilient ribs. A filter balloon is located between the catheter exterior and the ribs. Inflation of the filter balloon extends the ribs outward across the vessel to form a trap for fragments loosened by the dilatation balloon. When the filter balloon is deflated, the resilient ribs retract against the catheter to retain the fragments during withdrawal of the catheter.

Another prior art device provides an expandable occlusion member mounted on a slender, elongate wire. The occlusion member is placed distal to the intended treatment site and expanded to obstruct the flow of bodily fluids during the procedure. An interventional catheter is guided to the treatment site over the wire and the vessel narrowing is enlarged. Any emboli produced are trapped upstream of the occlusion balloon. Bodily fluid containing the particulate is aspirated from the vessel, either through a dedicated lumen in the treatment catheter, or via a separate aspiration catheter that has been exchanged for the treatment catheter. The occlusion member is then collapsed and removed from the patient. The occlusion member may be an inflatable balloon or a mechanically expandable structure covered by a non-porous membrane.

Another prior art device includes a filter mounted on the distal portion of a hollow guidewire or tube. A moveable core wire is used to open and close the filter. The filter is secured at the proximal end to the tube and at the distal end to the core wire. Pulling on the core wire while pushing on the tube draws the ends of the filter toward each other, causing the filter framework between the ends to expand outward into contact with the vessel wall. Filter mesh material is mounted to the filter framework. To collapse the filter, the procedure is reversed, i.e., pulling the tube proximally while pushing the core wire distally to force the filter ends apart.

Another prior art device has a filter made from a shape memory material. The device is deployed by moving the proximal end of the filter towards the distal end. The filter is collapsed by sliding a sheath over the filter and then withdrawn by removing the sheath and filter together.

Another prior art filter device includes a compressible polymeric foam filter mounted on a shaft that is inserted over a guidewire. The filter is inserted in a collapsed state within a housing which is then removed to deploy the filter once in position. The filter is retracted by inserting a large bore catheter over the shaft and the filter and then removing the shaft, filter and catheter together.

Another prior art filter arrangement has a filter comprised of a distal filter material secured to a proximal framework. This filter is deployed in an umbrella manner with a proximal member sliding along the shaft distally to open the filter and proximally to retract the filter. A large separate filter sheath can be slid onto the shaft and the filter can be withdrawn into the sheath for removal from the patient.

Other known prior art filters are secured to the distal end of a guidewire with a tubular shaft. Stoppers are placed on the guidewire proximal and distal of the filter, allowing the filter to move axially independently of the guidewire. Sheaths are used to deploy and compress the filter.

One problem with known filter arrangements is that the capture element has a large profile as measured at the distal and proximal end regions thereof. The large profile of the collapsed capture element creates stenosis-crossing problems and possible snagging as the capture element is withdrawn through a stent. In addition, the force required to pull the capture element back into the retrieval sheath is greater than that which would be required if the capture element had a smaller profile. In particular, the braided element is too thick at the end regions under the marker bands. Further, the braided element is too thick in the tapered portion of the end regions, causing these regions to resist lying snugly about the guidewire when collapsed. In other words, the end regions may bulge outwardly instead of collapsing flatly against the core wire.

The main factor contributing to the enlarged profile of the filter or capture element is the thickness of the filaments used to form the filter. The profile is increased in part because the filaments are grouped together in a relatively small area for connection to the core wire and the thickness of the filaments prevents an appropriate reduction in profile.

SUMMARY OF THE INVENTION

Therefore, needed in the art is a distal protection device including a distal protection element where at least a portion thereof is reduced in thickness. To achieve this goal, for example, the thickness of the individual filaments forming the distal protection element may be reduced or portions thereof may be removed entirely. This reduction in wall thickness provides a decrease in the collapsed profile of the distal protection element. This reduction in end region thickness does not adversely affect the radial strength of the current distal protection element or otherwise adversely affect its performance. However, the thinner end regions make the distal protection element easier to steer and to collapse into the retrieval sheath. Additionally, this reduced profile minimizes stenosis-crossing problems and possible snagging.

The present invention is a distal protection device and method for making a distal protection device. The distal protection device is for use in vascular procedures and includes a distal protection element that is constructed of a plurality of filaments braided to form a distal protection element with two end regions, where in one embodiment, each end region includes a taper region and a neck region. The capture element includes an expandable frame with a mesh attached thereto acting as the emboli filter. The distal protection element is sized sufficiently to expand and cover the cross sectional area of the vessel just distal to the intended treatment area. At least one of the filaments in the distal protection element has a reduced thickness in one or both of the end regions.

An alternative embodiment includes the selective removal of portions of the filaments to reduce the stiffness of the end regions.

Another alternative embodiment of the method for making the distal protection device includes heat treating the distal protection element either before or after reducing the thickness of selected filaments.

Another alternative embodiment of the distal protection device includes marker bands secured around portions of the end regions of the distal protection element.

Additional alternative embodiments of the method for making the distal protection device include reducing the filament thickness through electropolishing, photo etching, chemical etching, laser etching or acid pickling.

Additional alternative embodiments of the distal protection device include a distal protection element constructed of: metal wires (including nitinol or drawn-filled tubing (DFT) wires, or a combination of the two); thermoplastic polymers; thermoset polymers; ceramics; glass or any combinations thereof. Any distal protection element including drawn-filled tubing wires may optionally include DFT wire with the outer casing selectively removed and the inner core thickness reduced by one of the above-referenced reduction methods.

Additional alternative embodiments of the distal protection device include making different profiles of the reduced thickness filaments in one or both end regions of the distal protection element. The end region may be gradually tapered from a larger first thickness to a smaller second thickness. Alternatively, the tapered end region may have a stepped-down taper, a spiral taper, longitudinal striping or any combinations thereof.

An additional alternative embodiment of the method for making a reduced diameter distal protection device of the present invention includes braiding the distal protection element having a first and second end region and then collapsing the braided distal protection element. The filaments of the first end region are bonded together while holding the distal protection element in a collapsed configuration. The filaments of the second end region are bonded in a similar manner. Marker bands are then attached around the first and second end regions.

The distal protection device of the present invention has an overall reduced thickness when in its collapsed state, while maintaining radial strength of the distal protection element.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The foregoing and other features and advantages of the invention will be apparent from the following, more particular description of preferred embodiments of the invention, as illustrated in the accompanying drawings. These drawings are provided to explain the principles of the invention and to enable a person skilled in the art to make and use the invention. The drawings are not drawn to scale.

DETAILED DESCRIPTION OF THE INVENTION

A preferred embodiment of the present invention is now described with reference to the figures where like reference numbers indicate identical or functionally similar elements.

While specific configurations are discussed, it should be understood that this is done for illustrative purposes only. A person skilled in the relevant art will recognize that other configurations and arrangements can be used without departing from the spirit and scope of the invention.

Figure 1:
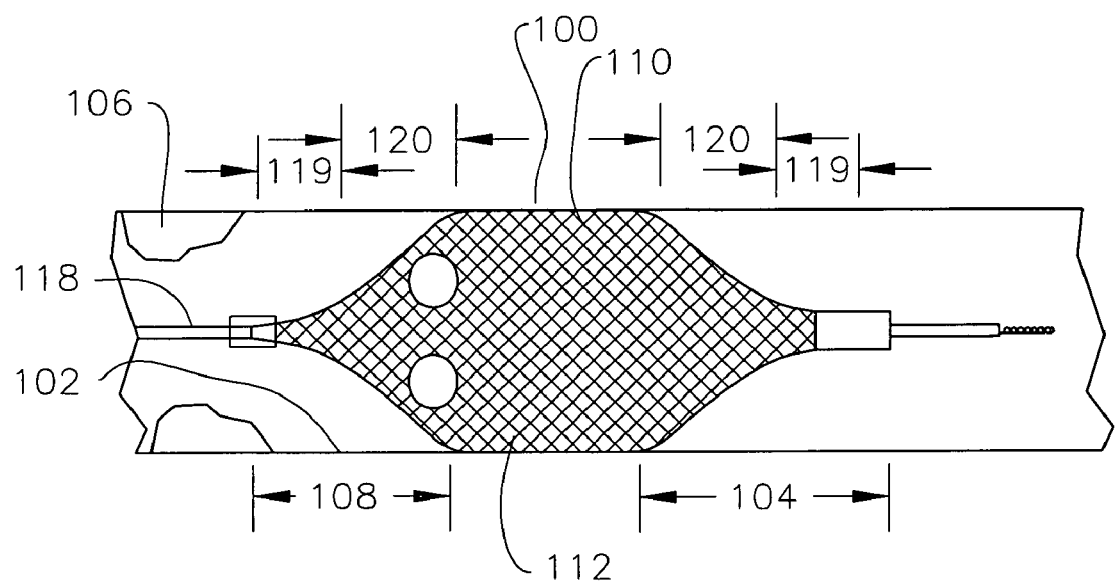
FIG. 1 illustrates a side view of a distal protection device of the present invention with the distal protection device shown deployed in a vessel.

Referring to FIG. 1, a distal protection device 100 is shown expanded or deployed in a vessel 102. Distal protection device 100 is for use in minimally invasive procedures, such as vascular procedures or other procedures where the practitioner desires to capture material that may be dislodged during the procedure. In one embodiment of the present invention, distal protection device 100 includes a distal protection element 110, a first marker band 114, a second marker band 116, and an elongate guidewire 118. In this embodiment, distal protection element 110 is a capture element or filter. In other embodiments, distal protection element may be an occluder. Capture element 110 is disposed about elongate guidewire 118 such that capture element 110 may be manipulated between a collapsed and an expanded configuration. One such configuration for manipulation of the capture element is described, for example, in U.S. Publication No. 2003-0135232 entitled "Temporary Intraluminal Filter Guidewire and Methods of Use", which is incorporated herein in its entirety by reference thereto.

In the embodiment shown in FIG. 1, capture element 110 is constructed by braiding a plurality of filaments 112 to form an enclosure with a first end region 104 and a second end region 108. First and second end regions 104, 108 each include a neck region 119 and a taper region 120. In another embodiment, end regions 104, 108 may include only neck region 119 or only taper region 120. Although shown as a frustum, taper region 120 can have any shape known in the art, such as, for example, hemispherical or parabolic. Capture element 110 is sized sufficiently to expand and cover a cross-sectional area of vessel 102 distal of intended treatment area 106.

First marker band 114 is attached to first end region 104 and second marker band 116 is attached to second end region 108. Marker bands 114 and 116 are typically attached about neck region 119 and are constructed of a radiopaque material and aid in the fluoroscopic observation of distal protection device 100 during manipulation thereof.

At least one of the filaments 112 in first end region 104, second end region 108 or both regions 104, 108 is reduced in thickness or a portion thereof is selectively removed, such as by cutting away a portion of filament 112, to produce a lower collapsed profile. Filaments 112 may be reduced in thickness either individually or all at once, as described further herein. Filaments 112 can be comprised of a variety of materials such as, for example, metal including stainless steel, nitinol, or drawn-filled tubing wires, thermoplastic polymers, thermoset polymers, ceramics or glass, either alone or in combination, e.g., forming a mesh of alternating nitinol and DFT wires. It will be apparent to those skilled in the relevant art that other materials could be used for filaments 112. If using a heat-set material, such as nitinol, filaments 112 may be heat treated either before or after reducing the thickness of the filaments 112.

Figure 2:
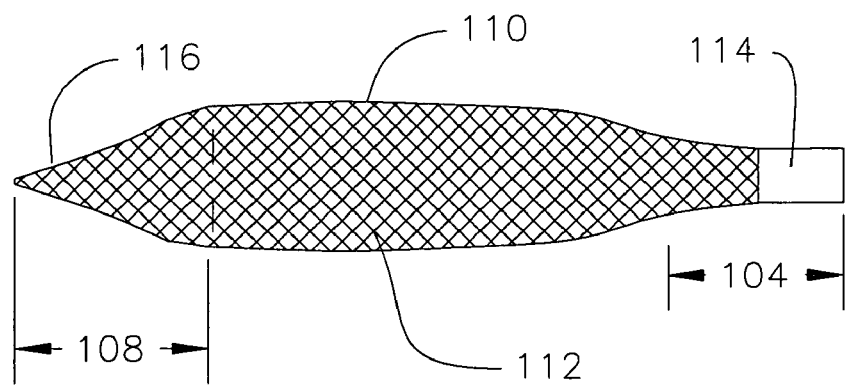
FIG. 2 illustrates a side view of a capture element of the present invention with the capture element shown in a collapsed profile.

FIG. 2 shows capture element 110 in its collapsed state. In one embodiment of the present invention, a lower collapsed profile can be achieved by bonding filaments 112 together in first end region 104 while the capture element 110 is in its collapsed state. For the purposes of example only, if using a heat-set material such as nitinol to form capture element 110, capture element 110 is typically heat set in the expanded configuration. In this configuration, those portions of filaments 112 disposed in first and second end regions 104, 108 are bunched together in a disordered manner. This bunched configuration increases unnecessarily the thickness of first and second end regions 104, 108. However, if capture element 110 is manipulated to a closed configuration, those portions of filaments 112 disposed in first and second end regions 104, 108 are pulled or pushed into a more orderly configuration. In this orderly configuration, filaments 112 tend to lie next to each other smoothly which creates a flatter, thinner profile. While in this expanded configuration, capture element 110 is bonded to guidewire 118 or to another structure to affix capture element 110 to guidwire, such as a sleeve slidably disposed on guidewire 118. The bonding agent maintains the flatter, thinner configuration even once capture element 110 is expanded. In addition, filaments 112 may be bonded together in second end region 108 while capture element 110 is in its collapsed state. First marker band 114 may then be attached to first end region 104 and second marker band 116 may then be attached to second end region 108.

Figure 3:
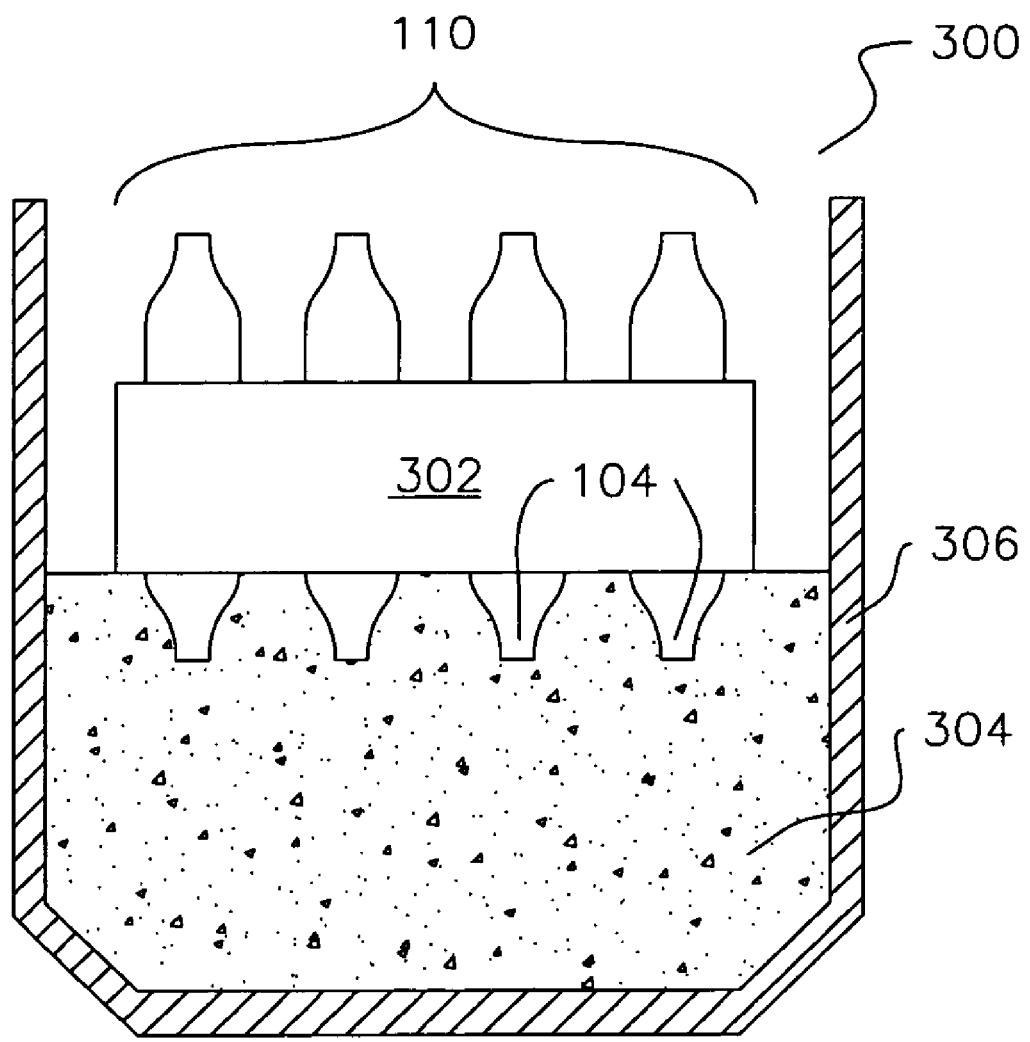
FIG. 3 illustrates several capture elements of the present invention in a chemical solution during manufacture.

The thickness of filaments 112 can be reduced by one or more of the following methods: electropolishing, photo etching, chemical etching, laser etching, mechanical grinding, or acid pickling. Referring to FIG. 3, a reducing apparatus 300 is shown that can be used in one embodiment for reducing the thicknesses of end regions 104, 108. In this embodiment, at least one of end regions 104, 108 are dipped into a chemical solution 304 contained in a solution container 306. Chemical solution 304 can be, for example, hydrochloric acid, sulfuric acid, sodium acid sulfate, polymeric solvent, or other appropriate solution.

In this embodiment, a capture element holder 302 is loaded with capture elements 110. As shown, capture element holder 302 may be constructed of chemically inert foam or some other buoyant material so that it maintains a portion of each capture element 110 at a position of constant exposure to chemical solution 304. Alternatively, capture element holder 302 may be fixed, either permanently or adjustably, to solution container 306.

Capture element holder 302 is placed in solution container 306 so that first end region 104 of each capture element 110 extends into chemical solution 304. While submerged in chemical solution 304, the submerged material of filaments 112 is slowly etched away such that the overall thickness of filaments 112 is reduced. After a specified period of time based upon the degree of desired etching or material reduction, capture element holder 302 is removed from chemical solution 304 and/or capture elements 110 are removed from capture element holder 302. The process may be repeated with second end region 108. Once material reduction is complete, each capture element 110 is affixed to a guidewire 118.

In another embodiment, where at least some of filaments 112 are DFT wires, the reduction in thickness may be accomplished by removing the outer casing such as, for example, by mechanical stripping. The DFT wire can be further reduced in thickness by removing a portion of the core of the DFT wire, such as by etching.

Figure 4:
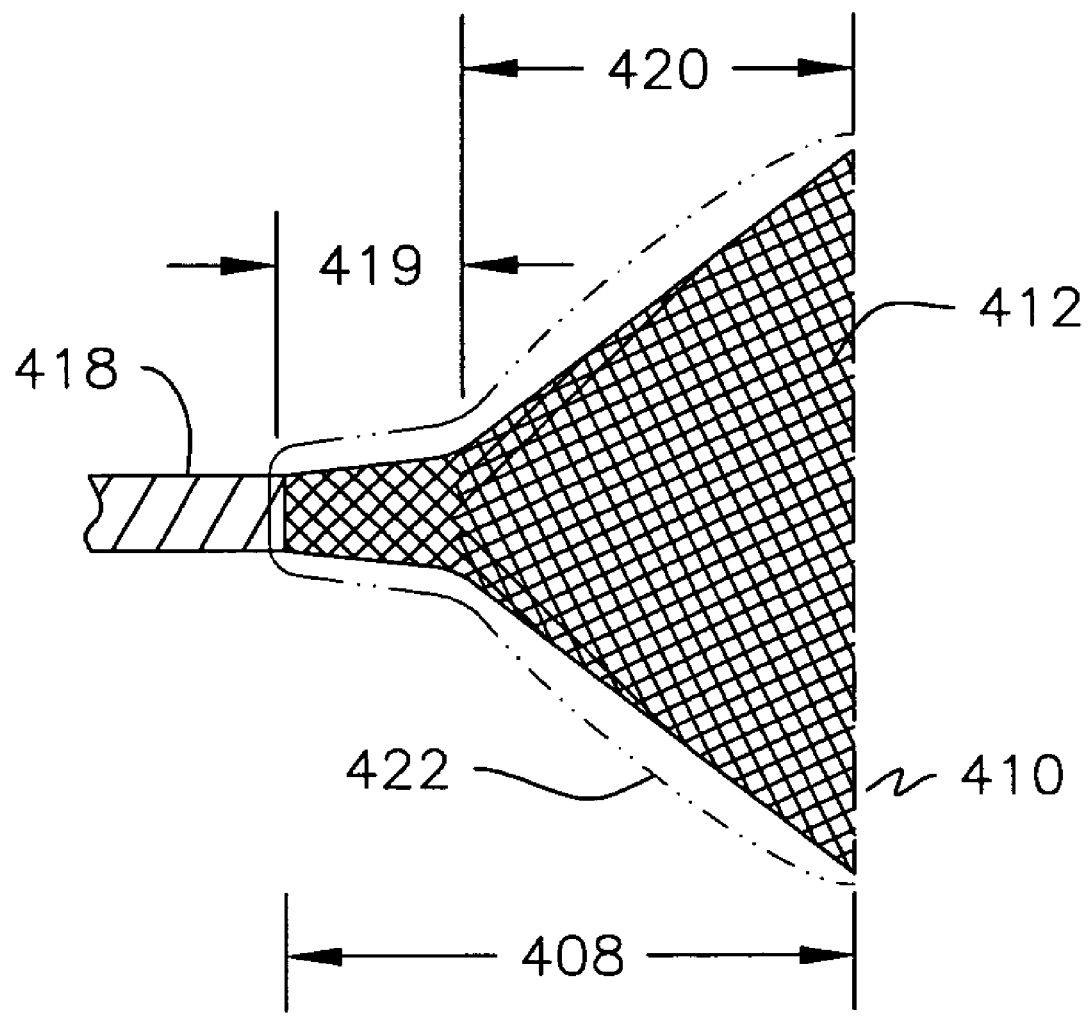
FIG. 4 illustrates a side view of a section of a distal protection device of the present invention with tapering in an end region of the capture element.
Figure 4A:
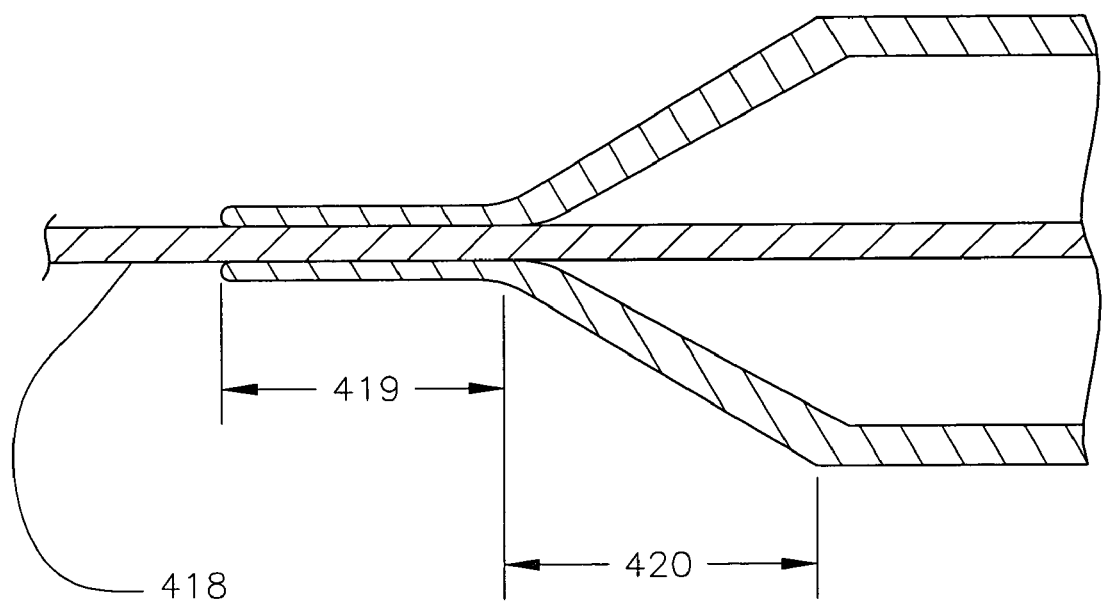
FIG. 4A illustrates a longitudinal cross-sectional side view of the distal protection device of FIG. 4.

Referring now to FIGS. 4-7, different embodiments of the present invention are shown. In all respects, save for the shape of the end regions, each of these embodiments is similar in material and construction to those described above with respect to FIG. 1. Referring now to FIG. 4, occluder 410 having a gradually diminished thickness in an end region 408 is shown as the distal protection element. Occluder 410 is a braided mesh similar to capture element 110, with a blood-impermeable material 411 such as rubber is affixed to the mesh to fill the interstitial spaces thereof to prevent blood from moving past occluder 410. A taper region 420 and a neck region 419, which in this embodiment comprise end region 408, are shown having reduced profiles. FIG. 4A shows a cross-sectional view of this embodiment. Neck region 419 and taper region 420 are shown to have gradually reduced thickness, with the thickest portion at a distal end of taper region 420 and the thinnest portion at a proximal end of neck region 419, where neck region 419 is attached to guidewire 418. The original thickness, i.e., the thickness prior to treatment of filaments 412, of end region 408 extended to phantom line 422. Not shown for the sake of clarity is a marker band which can be used to compress filaments 412 further in neck region 419.

The embodiment of FIG. 4 may be manufactured according to the method depicted in and described with reference to FIG. 3. For example, entire end region 408 may be inserted into a chemical bath so that all filaments 412 are reduced. End region 408 may then be slowly but steadily withdrawn from the chemical bath so that less material is removed in the withdrawn portions. After end region 408 has been processed to reduce the thickness thereof, occluder 410 is dipped into an elastomeric solution, such as liquid rubber. When this solution is cured, the interstitial spaces of the mesh are filled such that occluder 410 may still expand and contract like capture element 110 while forming a complete blockage within a vessel. Alternatively, a sheet of a suitable elastomeric material may be affixed to the mesh of occluder 410, such as by gluing.

Figure 5:
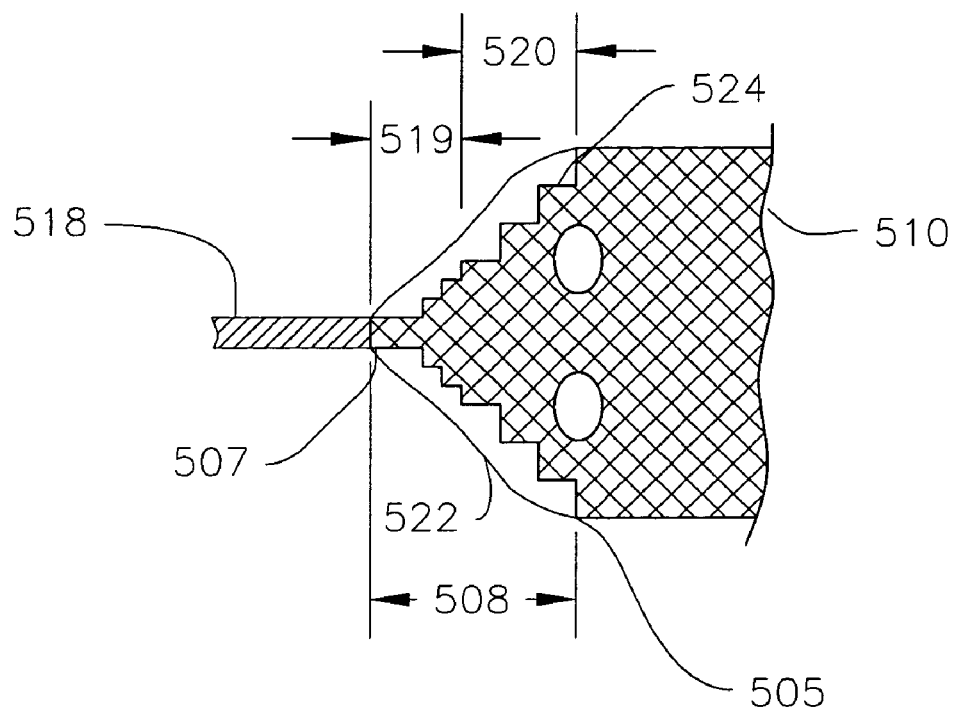
FIG. 5 illustrates a side view of a section of a first alternative embodiment of a distal protection device of the present invention with stepped tapering in an end region of the capture element.
Figure 5A:
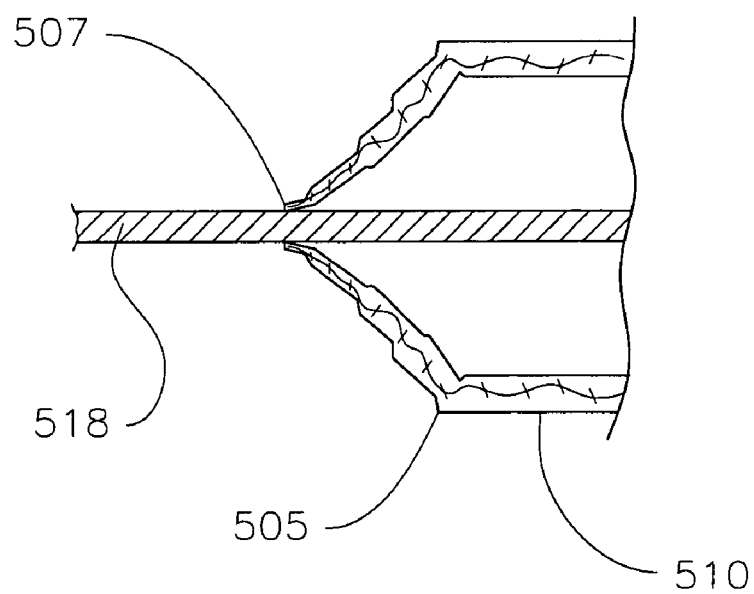
FIG. 5A illustrates a longitudinal cross-sectional side view of the distal protection device of FIG. 5.

FIG. 5 shows a second alternate embodiment of the present invention. In this embodiment, a capture element 510 includes a stepped-down end region 508. A taper region 520 and a neck region 519 are reduced in thickness step-wise from an original outer diameter shown with phantom line 522. The maximum thickness is at a taper region distal end 505, and the minimum thickness is at a neck region proximal end 507. As can be seen more clearly in FIG. 5A, the wall thickness of capture element 510 also decreases from a maximum point at taper region distal end 505 to a minimum point at neck region proximal end 507. A marker band, not shown, can then be placed around neck region 519, providing a further reduced profile in end region 508.

The embodiment shown in FIG. 5 may be manufactured using a slightly different process than that described above with respect to FIG. 4. In one embodiment, end region 508 is placed in a chemical bath, but to achieve the stepped effect, the thinnest portion, neck region 519, must remain in the chemical bath for a longer period of time than the thicker portions. For example, entire end region 508 may be placed in the chemical bath initially. After a specified duration, a length of end region 508 equal to the length of a distalmost step 524 is removed from the chemical bath. In this manner, the chemical bath continues to remove material from the portion of end region 508 remaining in the chemical bath, but no further material is removed from step 524 of end region 508, which has been extracted from the chemical bath. Repeating this process until all steps are formed and neck region 519 is the desired thickness completes the stepped profile of end region 508.

Alternatively, only neck region 519, or a portion thereof, is submerged into the chemical bath. After a specified duration, a second length of end region 508 equal to the length of a step 524 is submerged. This process continues until entire end region 508 is submerged in the chemical bath. In this manner, neck region 519 is submerged for the longest duration, so the greatest amount of material is removed therefrom. As each step remains in the chemical bath for a slightly different duration, different amounts of material are removed, thereby creating the stepped profile of end region 508.

Figure 6:
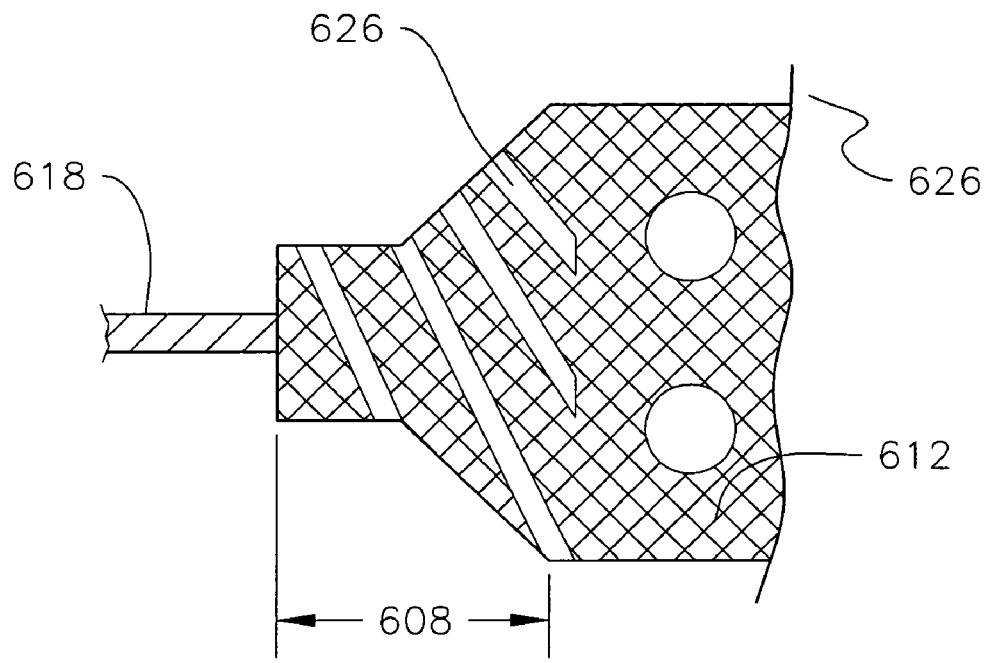
FIG. 6 illustrates a side view of a section of a second alternative embodiment of a distal protection device of the present invention with spiral tapering in an end region of the capture element.
Figure 6A:
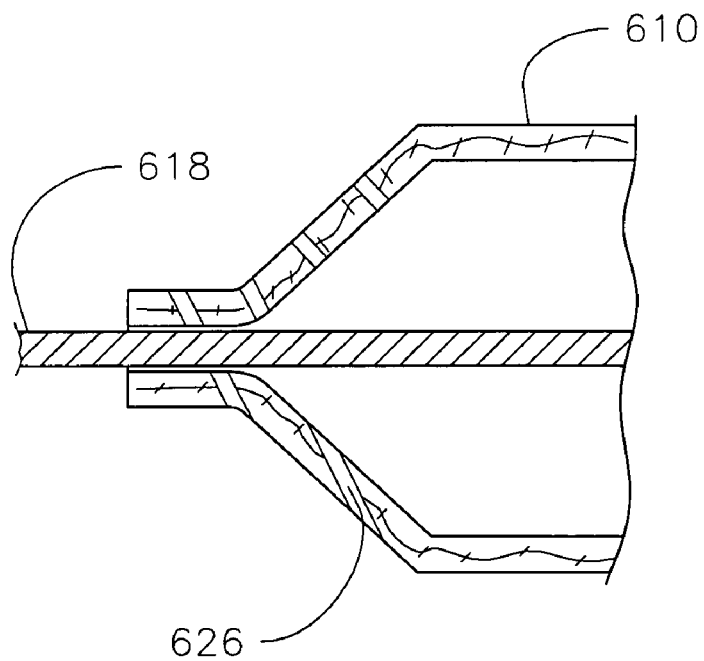
FIG. 6A illustrates a longitudinal cross-sectional side view of the distal protection device of FIG. 6.

FIG. 6 shows a third alternative embodiment of the present invention. In this embodiment, portions 626 of a capture element 610 are selectively removed from an end region 608 in a spiral pattern. As shown in FIG. 6A, select portions of filaments 612 are entirely removed. This removal of material from capture element 610 reduces the stiffness and increases the flexibility of end region 608, so that end region 608 is more easily manipulated into lying flat against a guidewire 618 for a lower collapsed profile.

The manufacture of end region 608 may be done with a chemical bath. In this embodiment, a material inert to the chemical bath is used to mask the spiral pattern prior to inserting end region 608 into the chemical bath. End region 608 remains in the chemical bath until portions 626 are removed entirely. Then, end region 608 is removed from the bath and the masking removed. Alternatively, a laser may be used to etch or cut away portions 626. In another alternative embodiment, a mechanical grinder may be used to remove the material from portions 626 in the appropriate pattern. In yet another alternative embodiment, a rubber sleeve having cutouts in the desired pattern is placed around end region 608, leaving exposed those portions adjacent the cutouts. End region 608 is then subjected to a vapor or acid pressure wash, which eats away the exposed material while leaving the material covered by the rubber sleeve intact. The rubber sleeve is then removed.

Figure 7:
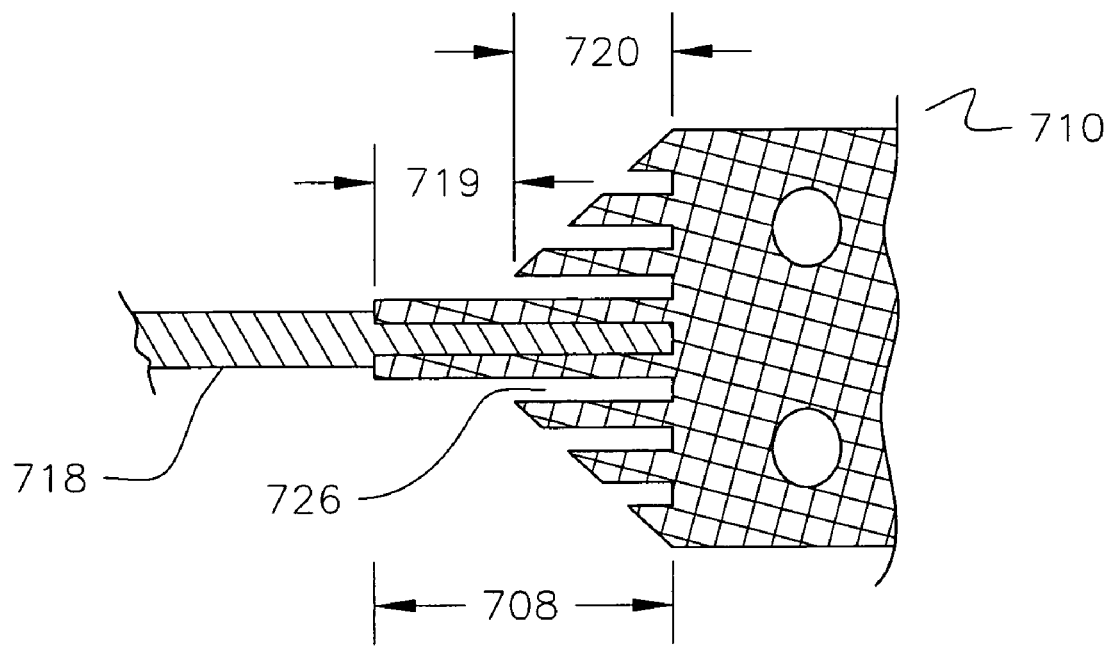
FIG. 7 illustrates a side view of a section of third alternative embodiment of a distal protection device of the present invention with longitudinal tapering in an end region of the capture element.

FIG. 7 shows a fourth alternative embodiment of the present invention.

Figure 8:
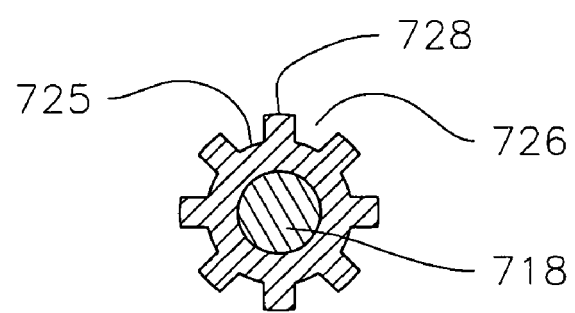
FIG. 8 illustrates an end view of the distal protection device of FIG. 7.

In this embodiment, longitudinal slots 726 are formed by selectively removing strips of capture element 710 from an end region 708. FIG. 8 is a cross-sectional end view end region 708 showing longitudinal ridges 728 are interspersed with longitudinal slots 726. As with the embodiment shown in FIG. 6, this removal of material from capture element 710 results in decreased stiffness and increased flexibility of end region 708. Further, if a marker band (not shown) is placed around a neck region 719 of end region 708, the marker band may be used to compress longitudinal ridges 728 into longitudinal slots 726, e.g., by folding or deforming longitudinal ridges 728, thereby providing a reduced overall profile in neck region 719.

The manufacture of end region 708 may be achieved in a manner similar to that described above with respect to the manufacture of end region 608. In this embodiment, however, the material removed by the chemical bath, laser, or mechanical grinder follows a striped pattern instead of the spiral pattern of end region 608.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art. All patents and publications described herein are incorporated in their entirety by reference thereto.

What is claimed is:

1. A method for manufacturing a distal protection element for preventing emboli in a blood vessel from moving away from a treatment site during a vascular procedure, the method comprising:
    braiding a plurality of filaments to form an enclosure;
    forming the braided enclosure to have a first end region and a second end region, each of the first and second end regions having a taper region and a neck region adapted for attachment to a guidewire; and
    after the step of forming the braided enclosure, simultaneously reducing a thickness of all of the filaments of the braided enclosure along at least a portion of the first end region.

2. The method of claim 1, further comprising: heat treating the filaments of the braided distal protection element.

3. The method of claim 2, wherein the heat treating step is performed prior to the reducing step.

4. The method of claim 2, wherein the heat treating step is performed after the reducing step.

5. The method of claim 1, wherein the distal protection element is a capture element.

6. The method of claim 1, wherein the distal protection element is an occluder.

7. The method of claim 1, wherein the reducing step comprises electropolishing the filaments along at least a portion of each of the filaments.

8. The method of claim 1, wherein the reducing step comprises etching the filaments along at least a portion of each of the filaments.

9. The method of claim 8, wherein the etching step is selected from the group consisting of photo etching, chemical etching and laser etching.

10. The method of claim 1, wherein the reducing step comprises acid pickling the filaments along at least a portion of each of the filaments.

11. The method of claim 1, wherein the reducing step comprises mechanically grinding the filaments along at least a portion of each of the filaments.

12. The method of claim 1, wherein the filaments comprise nitinol wires.

13. The method of claim 1, wherein the filaments comprise drawn-filled tubing wires.

14. The method of claim 1, wherein the filaments comprise a combination of nitinol wires and drawn-filled tubing wires.

15. The method of claim 1, wherein the filaments are made of material selected from the group consisting of metal, thermoplastic polymer, thermoset polymer, ceramics and glass.

16. The method of claim 1, wherein the reducing step creates a gradual decrease in the thickness of the filaments along at least a portion of the first end region of the braided enclosure.

17. The method of claim 1, wherein the reducing step creates a stepped profile in the thickness of the filaments along at least a portion of the first end region of the braided enclosure.

18. The method of claim 1, wherein the reducing step creates a decrease in the thickness of the filaments along the neck region of the first end region of the braided enclosure.

19. The method of claim 18, wherein the reducing step also creates a decrease in the thickness of the filaments along the taper region of the first end region of the braided enclosure.

* * * * *